(12) United States Patent
Winston et al.

(10) Patent No.: US 11,213,393 B2
(45) Date of Patent: Jan. 4, 2022

(54) COMPRESSIBLE HEART VALVE ANNULUS SIZING TEMPLATES

(75) Inventors: Matthew T. Winston, Rancho Santa Margarita, CA (US); Da-Yu Chang, Irvine, CA (US); Louis A. Campbell, Santa Ana, CA (US); James A. Davidson, San Juan Capistrano, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 1663 days.

(21) Appl. No.: 13/429,123

(22) Filed: Mar. 23, 2012

(65) Prior Publication Data
US 2012/0253457 A1 Oct. 4, 2012

Related U.S. Application Data

(60) Provisional application No. 61/470,658, filed on Apr. 1, 2011.

(51) Int. Cl.
*A61F 2/24* (2006.01)
(52) U.S. Cl.
CPC .... *A61F 2/2496* (2013.01); *A61F 2250/0087* (2013.01); *A61F 2250/0091* (2013.01)
(58) Field of Classification Search
CPC ............ A61F 2/2496; A61F 2250/0087; A61F 2250/0091
See application file for complete search history.

(56) References Cited

U.S. PATENT DOCUMENTS

| 3,164,009 A | 1/1965 | Schaschl |
| 4,016,867 A | 4/1977 | King et al. |
| 4,185,638 A | 1/1980 | Bruner |
| 4,362,167 A | 12/1982 | Nicolai et al. |

(Continued)

FOREIGN PATENT DOCUMENTS

| DE | 29911694 U1 | 8/1999 |
| WO | 9640006 A1 | 12/1996 |

(Continued)

OTHER PUBLICATIONS

Techniques for 3D Quantitative Echocardiography, University of Washington Cardiovascular Research & Training Center Cardiac Imaging Research Lab, pp. 1-5, Oct. 2003.

(Continued)

*Primary Examiner* — Rene T Towa
(74) *Attorney, Agent, or Firm* — Guy Cumberbatch

(57) ABSTRACT

Compressible heart valve annulus sizing templates suitable for minimally-invasive or otherwise reduced accessibility surgeries. The sizing templates may be folded, rolled, or otherwise compressed into a reduced configuration for passage through an access tube or other such access channel. Once expelled from the access tube the sizing templates expand to their original shape for use in sizing the annulus. The templates may be formed of an elastomeric polymer material such as silicone, a highly elastic metal such as NITINOL, or both. Grasping tabs or connectors for handles permit manipulation from outside the body. A NITINOL wireform may be compressed for passage through an access tube and expelled from the distal end thereof into a cloth cover to assume a sizer shape.

12 Claims, 5 Drawing Sheets

(56) References Cited

U.S. PATENT DOCUMENTS

| | | | |
|---|---|---|---|
| 4,489,446 A * | 12/1984 | Reed | A61F 2/2448 137/846 |
| 4,566,465 A | 1/1986 | Arhan et al. | |
| 4,643,194 A | 2/1987 | Fogarty | |
| 4,914,097 A | 4/1990 | Oda et al. | |
| 5,010,892 A | 4/1991 | Colvin et al. | |
| 5,061,277 A * | 10/1991 | Carpentier | A61F 2/2448 623/2.36 |
| 5,316,016 A | 5/1994 | Adams et al. | |
| 5,350,420 A * | 9/1994 | Cosgrove | A61F 2/2427 623/2.11 |
| 5,396,887 A | 3/1995 | Imran | |
| 5,533,515 A | 7/1996 | Coller et al. | |
| 5,573,007 A | 11/1996 | Bobo, Sr. | |
| 5,728,064 A | 3/1998 | Burns et al. | |
| 5,752,522 A | 5/1998 | Murphy | |
| 5,814,098 A | 9/1998 | Hinnenkamp et al. | |
| 5,848,969 A | 12/1998 | Panescu et al. | |
| 5,855,563 A | 1/1999 | Kaplan et al. | |
| 5,865,801 A | 2/1999 | Houser | |
| 5,885,228 A | 3/1999 | Rosenman et al. | |
| 5,919,147 A | 7/1999 | Jain | |
| 5,921,934 A | 7/1999 | Teo | |
| 5,921,935 A | 7/1999 | Hickey | |
| 6,010,511 A | 1/2000 | Murphy | |
| 6,019,739 A | 2/2000 | Rhee et al. | |
| 6,081,737 A | 6/2000 | Shah | |
| 6,083,179 A | 7/2000 | Oredsson | |
| 6,099,475 A | 8/2000 | Seward et al. | |
| 6,110,200 A | 8/2000 | Hinnenkamp | |
| 6,136,017 A | 10/2000 | Craver et al. | |
| 6,319,281 B1 | 11/2001 | Patel | |
| 6,322,526 B1 | 11/2001 | Rosenman et al. | |
| 6,350,281 B1 | 2/2002 | Rhee | |
| 6,406,493 B1 * | 6/2002 | Tu | A61F 2/2448 623/2.37 |
| 6,582,419 B1 | 6/2003 | Schoon et al. | |
| 6,598,307 B2 | 7/2003 | Love et al. | |
| 6,786,924 B2 * | 9/2004 | Ryan et al. | 623/2.36 |
| 6,802,860 B2 | 10/2004 | Cosgrove et al. | |
| 6,942,694 B2 | 9/2005 | Liddicoat et al. | |
| 6,955,689 B2 * | 10/2005 | Ryan | A61F 2/2445 623/2.36 |
| 7,258,698 B2 | 8/2007 | Lemmon | |
| 2002/0020074 A1 | 2/2002 | Love et al. | |
| 2002/0055773 A1 | 5/2002 | Campbell et al. | |
| 2002/0173842 A1 * | 11/2002 | Buchanan | A61F 2/2409 623/2.14 |
| 2003/0045929 A1 * | 3/2003 | McCarthy | A61F 2/2445 623/2.37 |
| 2003/0191416 A1 | 10/2003 | Rosenman et al. | |
| 2004/0215235 A1 | 10/2004 | Jackson et al. | |
| 2004/0237321 A1 | 12/2004 | Rudko et al. | |
| 2005/0085904 A1 * | 4/2005 | Lemmon | A61F 2/2427 623/2.11 |
| 2006/0195134 A1 | 8/2006 | Crittenden | |
| 2006/0247764 A1 * | 11/2006 | Annest | A61B 5/1076 623/3.1 |
| 2007/0299513 A1 | 12/2007 | Ryan et al. | |
| 2008/0009746 A1 | 1/2008 | Forster et al. | |
| 2008/0208331 A1 | 8/2008 | McCarthy et al. | |
| 2009/0069890 A1 | 3/2009 | Suri et al. | |
| 2009/0093877 A1 | 4/2009 | Keidar et al. | |
| 2009/0132036 A1 * | 5/2009 | Navia | 623/2.36 |
| 2009/0182419 A1 | 7/2009 | Bolling | |
| 2009/0192600 A1 | 7/2009 | Ryan | |
| 2009/0192602 A1 * | 7/2009 | Kuehn | A61F 2/2496 623/2.11 |
| 2009/0192603 A1 | 7/2009 | Ryan | |
| 2009/0192604 A1 | 7/2009 | Gloss | |
| 2009/0192605 A1 | 7/2009 | Gloss et al. | |
| 2010/0152844 A1 | 6/2010 | Couetil | |
| 2012/0071968 A1 * | 3/2012 | Li | A61F 2/2496 623/2.11 |

FOREIGN PATENT DOCUMENTS

| | | |
|---|---|---|
| WO | 9741801 A1 | 11/1997 |
| WO | 9742871 A1 | 11/1997 |
| WO | 2010111621 A1 | 9/2010 |

OTHER PUBLICATIONS

International Search Report from corresponding International Application No. PCT/US2012/030660 dated Oct. 25, 2012.

* cited by examiner

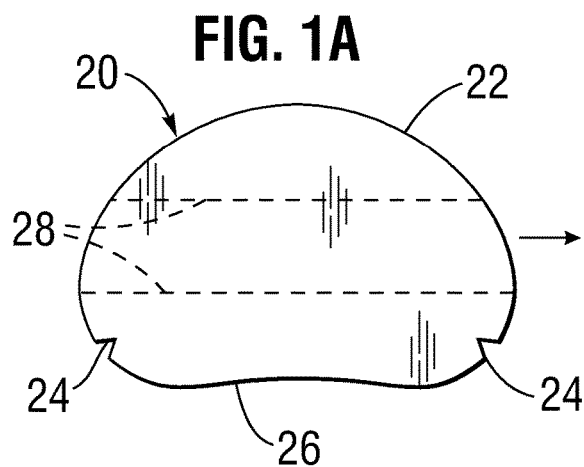
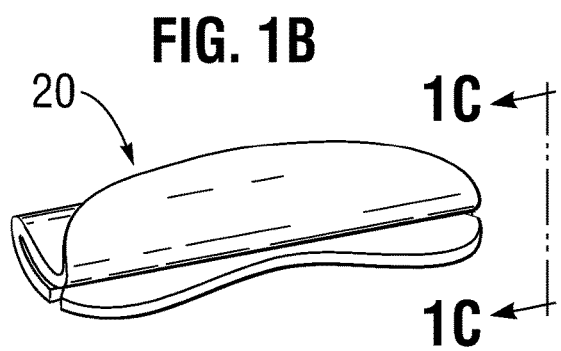
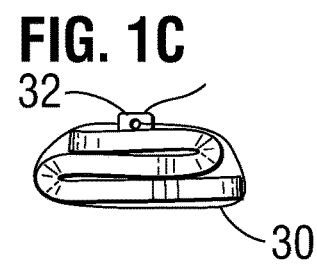
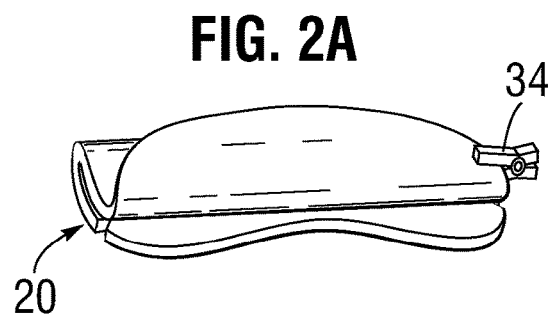
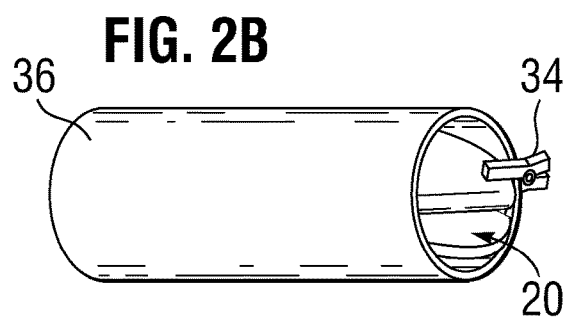
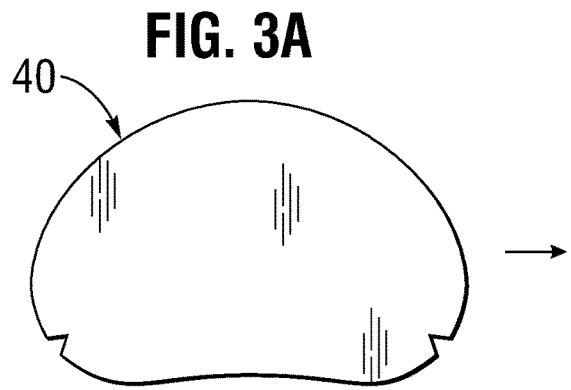
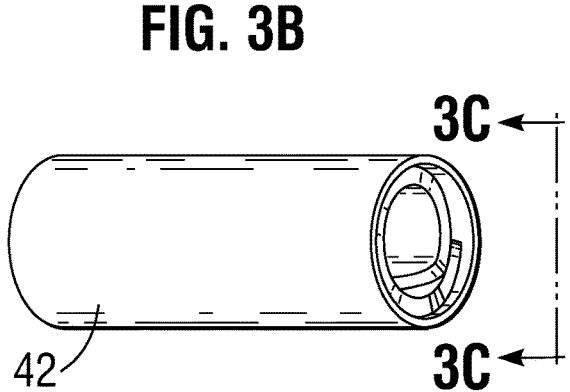
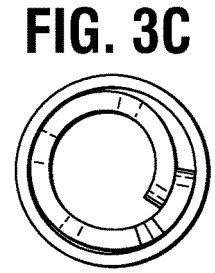

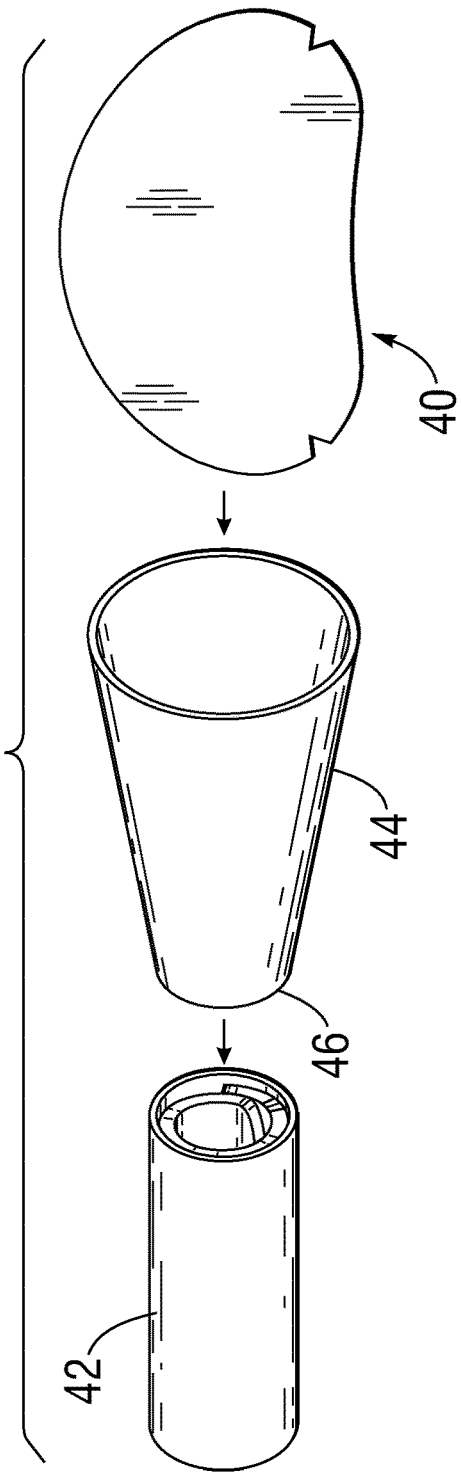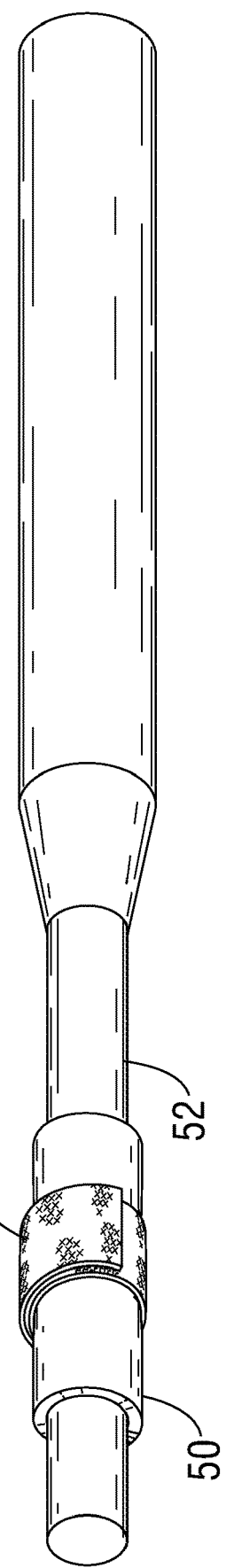

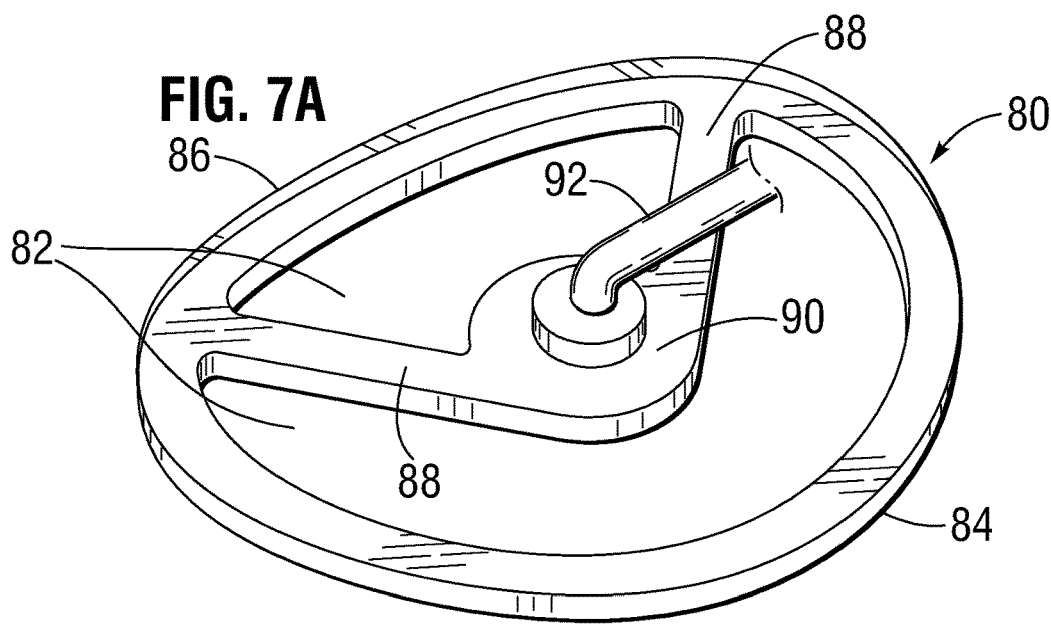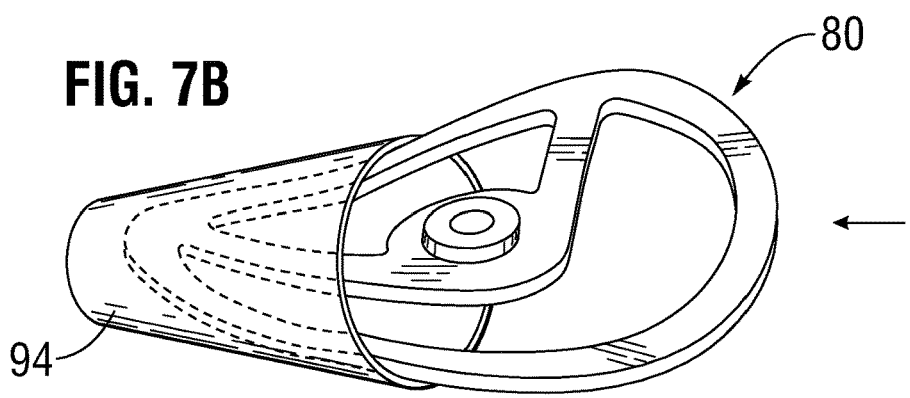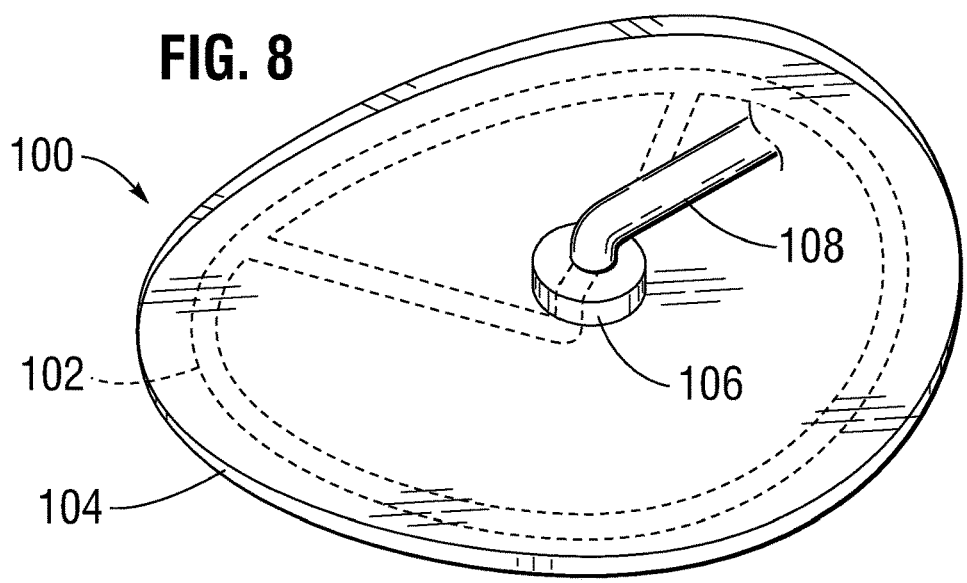

COMPRESSIBLE HEART VALVE ANNULUS SIZING TEMPLATES

RELATED APPLICATIONS

The present application claims priority to U.S. Provisional Application No. 61/470,658, filed Apr. 1, 2011, which is incorporated herein by reference.

FIELD OF THE INVENTION

The present invention generally relates to anatomical orifice sizers and, more particularly, to sizing templates for heart valve annuluses that may be deployed through access devices, and methods of use.

BACKGROUND OF THE INVENTION

In vertebrate animals, the heart is a hollow muscular organ having four pumping chambers: the left and right atria and the left and right ventricles, each provided with its own one-way valve. The natural heart valves are identified as the aortic, mitral (or bicuspid), tricuspid and pulmonary, each having flexible flow-occluding leaflets mounted to a surrounding annulus comprising dense fibrous rings that attach either directly or indirectly to the atrial and ventricular muscle fibers. Each annulus defines a flow orifice.

Heart valve disease is a widespread condition in which one or more of the valves of the heart fails to function properly. Diseased heart valves may be categorized as either stenotic, wherein the valve does not open sufficiently to allow adequate forward flow of blood through the valve, and/or incompetent, wherein the valve does not close completely, causing excessive backward flow of blood or regurgitation through the valve when the leaflets are supposed to coapt together. Valve disease can be severely debilitating and even fatal if left untreated.

Various surgical techniques may be used to repair a diseased or damaged valve. In a valve replacement operation, the damaged leaflets are excised and the annulus sculpted to receive a replacement valve. Another less drastic method for treating defective valves is through repair or reconstruction, which is typically used on minimally calcified valves. One repair technique that has been shown to be effective in treating incompetence is annuloplasty, in which the deformed valve annulus is reshaped by attaching a prosthetic annuloplasty repair segment or ring to the valve annulus. The annuloplasty ring is designed to support the functional changes that occur during the cardiac cycle: maintaining leaflet coaptation and valve integrity to prevent regurgitation while permitting good hemodynamics during forward flow.

To perform successful valve replacement and annuloplasty surgeries, the size of the valve annulus must be accurately measured. Sizing may be achieved by measuring the width and the height of the anterior leaflet of the mitral valve, for example, using a valve sizer or template, which resembles the shape of the valve annulus and is provided in various incremental sizes corresponding to the stepped valve or ring sizes. In order to use a sizing template, a surgeon estimates the valve annulus size and selects the template accordingly. The template is guided into proximity of the annulus with a handle. If the template is not judged to be the correct size, it is withdrawn, and replaced by a different template. Once the size of the annulus has been determined, a properly sized valve or annuloplasty device may be selected and implanted.

Surgical techniques for annuloplasty surgery are typically performed open-chest. This usually requires the patient to be placed on a cardiac bypass machine to pump and oxygenate the blood while the surgeon operates on the stopped heart muscle. Open-chest surgery can be very traumatic for the patient and recovery can take many months. Additionally, such surgery may not be an option for some patients due to limited possibility for recovery, concurrent disease, or age.

In recent years, advancements in "minimally-invasive" surgery and interventional cardiology have encouraged some investigators to pursue direct access port surgeries and percutaneous replacement of heart valves. Similarly, less invasive annuloplasty implant procedures have been developed. However, these procedures reduce the available space to deliver surgical instruments to a surgical site, and reduce the space in which surgical instruments may be operated within the area of the surgical site. Traditional annuloplasty and valve sizing and holding instruments are designed for use with open-chest surgery that exposes the implant site. Such instruments will not fit through significantly reduced surgical field access points or passages. Some valve sizing templates for less invasive procedures have been disclosed, including those in U.S. Patent Publication No. 2009/0192602 to Kuehn, et al.

Despite the current existence of sizing devices for sizing a valve annulus, there is still a need for improved devices, and in particular those devices that may be used during less-invasive cardiac surgical procedures.

SUMMARY OF THE INVENTION

In accordance with a first embodiment, the present application presents a heart valve annulus sizing template comprising a compressible body having a peripheral plan view shape of a target heart valve annulus and a thickness between about 0.3-3.0 mm. An inner skeleton is embedded within the compressible body and is formed of a material more rigid than the material of the compressible body. The inner skeleton may comprise an outer peripheral ring in plan view shaped like a target heart valve annulus and a plurality of spokes extending inward therefrom. The compressible body may be elastomeric, such as silicone, or an inelastic polymer. In one embodiment, the compressible body comprises a solid member extending across the periphery thereof.

Another aspect of the application is a heart valve annulus sizing template comprising a solid compressible body having a peripheral plan view shape of a target heart valve annulus and a thickness between about 0.3-3.0 mm. The sizing template further includes an inner fabric reinforcement member embedded within the compressible body. The template may also have a fabric grasping tab projecting away from one side of the compressible body integrally formed with the inner fabric reinforcement member. Alternatively, the template has a grasping tab integrally molded with and projecting away from one side of the compressible body. Preferably, the compressible body is plate-like member having a periphery sized to approximate the mitral annulus, and the inner fabric reinforcement member is generally planar and sized slightly smaller than the plate-like member.

Another heart valve annulus sizing template disclosed herein includes an elastomeric, compressible body having an outer peripheral ring in plan view shaped like a target heart valve annulus and a plurality of spokes extending inward therefrom to define visibility windows through the compressible body. A central hub is provided to which the spokes connect. The peripheral ring may be shaped to match the shape of the mitral annulus with a convex posterior side opposite a relatively straight or less convex anterior side, and wherein there are two spokes that generally project toward trigone corners between the posterior and anterior sides. The material of the compressible body is desirably transparent and includes a highly visible marker line circumscribing the outer peripheral ring. In one version, the highly visible marker line is color-coded depending on the size of annulus being measured.

A still further heart valve annulus sizing template of the present application comprises a compressible elastic wireform having an expanded shape of a target valve annulus and a compressed shape of smaller profile. An access tube is provided through which the wireform in its compressed shape may be advanced. The template further has a cloth cover attached to a distal end of the access tube and having an inner volume and shape that closely receives the wireform in its expanded shape. The expanded shape of the wireform may conform to a mitral annulus such that it has a convex posterior side opposite a relatively straight or less convex anterior side. The expanded shape of the wireform further may include a pair of trigone notches at the intersections of the posterior and anterior sides, wherein the wireform is darkly colored to contrast with a light colored cloth cover.

The present application also discloses a method of sizing a heart valve annulus comprising first providing a compressible annulus sizing template including an elastomeric body in the shape of a target valve annulus. The annulus sizing template is passed through a constrictor to reduce its profile, and constrained in its reduced profile configuration. The reduced profile annulus sizing template is then advanced to a target annulus, whereupon the constraints are released so that the annulus sizing template expands to an original shape. Finally, the annulus sizing template in its expanded configuration is manipulated to size the target valve annulus.

A further method of sizing a heart valve annulus disclosed herein comprises providing a foldable annulus sizing template including an elastomeric body in the shape of a target valve annulus. A technician folds the annulus sizing template to reduce its profile, and constrains the annulus sizing template in its reduced profile configuration. The reduced profile annulus sizing template is then advanced to a target annulus, whereupon the constraints are released so that the annulus sizing template expands to an original shape. Finally, the annulus sizing template in its expanded configuration is manipulated to size the target valve annulus. In one embodiment, the foldable annulus sizing template has a shape in plan view of a mitral valve annulus, and further includes fold lines provided thereon generally parallel to a major axis of the sizing template.

Another method of sizing a heart valve annulus includes providing a compressible annulus sizing template including an elastic wireform having a distal end in the shape of a target valve annulus. A technician passes the elastic wireform into an access tube to reduce its profile, and then advances the reduced profile elastic wireform to a target annulus. The distal end of the elastic wireform is expelled from the access tube into a surrounding cloth cover such that the distal end expands and assumes its original shape of the target valve annulus within the cloth cover. Finally, the annulus sizing template in its expanded configuration is manipulated to size the target valve annulus. The cloth cover is desirably secured to a distal end of the access tube.

A further understanding of the nature and advantages of the present invention are set forth in the following description and claims, particularly when considered in conjunction with the accompanying drawings in which like parts bear like reference numerals.

BRIEF DESCRIPTION OF THE DRAWINGS

The invention will now be explained and other advantages and features will appear with reference to the accompanying schematic drawings wherein:

FIG. 1A is a plan view of an exemplary flexible annuloplasty ring sizing template of the present application, and FIGS. 1B and 1C illustrate the template folded into a smaller delivery profile;

FIG. 2A shows a folded flexible annuloplasty ring sizing template held together with a clip, and FIG. 2B shows the clipped template place within an access tube;

FIG. 3A is a plan view of an alternative flexible annuloplasty ring sizing template of the present application, and FIGS. 3B and 3C illustrate the template rolled into a smaller delivery profile and placed within an access tube;

FIG. 4 illustrates one method for compressing a flexible annuloplasty ring sizing template into a smaller profile for introduction within an access tube;

FIG. 5 shows a rolled annuloplasty ring sizing template wrapped around a delivery handle and held with a strap;

FIG. 7A is a perspective view of a still further flexible annuloplasty ring sizing template of the present application formed of an elastomeric material and having visibility windows, and FIG. 7B is a schematic view of the sizing template being extruded through a compression cone;

FIG. 8 is a perspective view of a solid elastomeric annuloplasty ring sizing template having an internal more rigid skeleton;

DETAILED DESCRIPTION OF THE PREFERRED EMBODIMENTS

Figure 6A:
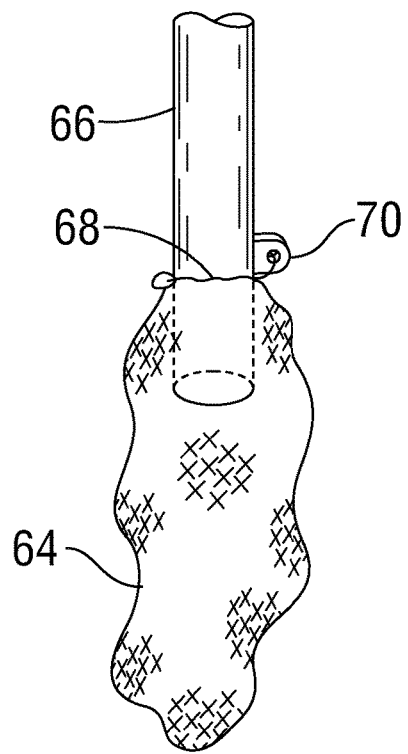
FIGS. 6A-6C are various views of an alternative flexible annuloplasty ring sizing template comprising a compressible wireform surrounded by a cloth cover being expelled from a distal end of an access tube.

Embodiments of the present invention include heart valve annulus sizing templates, and attendant delivery devices that are made, configured and/or may be manipulated to fit through significantly reduced surgical field access points and may be used in reduced surgical fields of operation. In particular, the sizing templates are deformable such that the devices may deform, bend or flex in order to fit through reduced surgical field access points. The sizing templates are preferably made to be attached and detached from the delivery devices of the present invention, however they may also be permanently attached thereto. Furthermore, heart valve surgeries carried out through reduced size access channels may benefit greatly from the assistance of robotic manipulators. The templates of the present invention are particularly well-suited to be passed through access passages and manipulated using robotic graspers and the like.

The sizing templates and delivery devices will be discussed with regard to their use during annuloplasty surgery. During annuloplasty surgery, the purpose of the delivery device is to first deliver a sizing template to a valve annulus that is in need of repair in order to size the annulus, and then after removal of the sizing template from the body, a holder with an attached annuloplasty ring is advanced and anchored to the valve annulus. Although the present application addresses annuloplasty surgery, it is contemplated that the present invention or features thereof may be used during other minimally invasive surgical procedures as well.

It should be understood that the various materials, shapes, and configurations of all the sizing templates described herein may be interchangeable. For example, a description of a ball and socket handle connection below may be transferred to other templates than the one for which it is described. Likewise, unless mutually exclusive, any of the delivery methodologies described herein may be utilized for each of the templates with similar results.

FIG. 1A shows a first exemplary flexible annuloplasty ring sizing template 20 of the present application in plan view. As seen in FIGS. 1B and 1C, the template 20 has a relatively small thickness and is flexible. The template 20 defines a modified D-shape mimicking the normal outline of a mitral annulus. It is the mitral valve that most often requires repair, but it should be understood that the present templates may be used to size other of the heart's annuluses, such as the tricuspid annulus. In the illustrated embodiment, the template 20 includes a convex posterior edge 22 that extends approximately three-quarters around the entire periphery and is delineated by a pair of trigone-marking notches 24. The posterior edge 22 matches the posterior aspect of the mitral annulus. The rest of the peripheral edge of the template 20, or anterior edge 26, forms an uneven somewhat concave shape that matches the anterior aspect of the mitral annulus. In a preferred embodiment, the plan view size of the template 20 conforms to the size of traditional sizers for annuloplasty rings where the major axis ranges between about 24 mm to about 40 mm. The thickness of the template 20 desirably ranges between about 0.3-3.0 millimeters, which may depend on the material, preferably silicone.

FIG. 1A indicates in phantom a pair of parallel fold lines 28 along which the template 20 may be folded as indicated in FIGS. 1B and 1C. The fold lines 28 may be perforations or other indentations to ensure folding along those lines, or may be simply marked on the surface of the template 20 to assist a technician when collapsing the template. In general, the template 20 is folded along one or more lines parallel to its major axis, which extends across the widest dimension of the plan view. In the illustrated embodiment, the template 20 is collapsed by folding twice so as to have three flaps that lie against one another, as seen in the view of FIG. 1C. Additionally, a suture thread 30 anchored to an eyelet 32 may be used to secure the template 20 in its folded configuration. The eyelet 32 also provides an anchor for a delivery handle or other such grasper to manipulate the template 20 once in the body and permitted to expand.

In use, a technician folds the template 20 into its reduced profile configuration of FIGS. 1B and 1C, and then inserts the template into an access tube or other such vehicle. The delivery tube enters the body through a direct access aperture, such as through a port formed in the chest directly over the heart. Alternatively, the surgery may require a mini thoracotomy which is more invasive than ports but less invasive than a full thoracotomy (open-heart procedure). Using forceps or a special grasper (not shown), the folded template 20 passes through the access tube and is expelled therefrom adjacent the mitral annulus. At this point, the flexibility of the material of the template 20 causes it to expand once released from the access tube, and after severing the securing suture thread 30, if present. Using the aforementioned forceps or grasper, the surgeon then manipulates the template 20 into proper position within the mitral annulus and determines the size of the annulus relative thereto. If necessary, the template 20 is removed from the surgical site, and a differently sized template introduced for more accuracy.

The sizing template 20 (as well as any other templates described herein) is preferably made from biocompatible material that is flexible or deformable. The flexible material is also preferably optically transparent, but could also be opaque. Some particular materials that may be used include a number of polymers and elastomers, including, but not limited to, polyurethanes and silicones. The flexible material may be compounded with a ferrous metal to achieve magnetic properties or any other radiopaque material for identification under x-ray. Also, the material could comprise a shape memory polymer or metal, such as NITINOL, for example. Other similar materials having such similar properties are also contemplated by the present invention. The material is preferably able to regain its predefined shape after being deformed in some way.

FIG. 2A shows the folded flexible annuloplasty ring sizing template 20 held together with a clip 34, rather than a suture. The clip 34 may be tethered to suture (not shown), and may be provided in a variety of configurations, including a clothespin-type as shown, or a simple U clip that fits closely around the outside of the folded contour. FIG. 2B shows the clipped template 20 place within an access tube 36 for delivery to the implantation site.

FIG. 3A illustrates an alternative flexible annuloplasty ring sizing template 40 of the present application, and FIGS. 3B and 3C illustrate the template spirally rolled into a smaller delivery profile and placed within an access tube 42. The template 40 may be configured the same as the earlier-describe template 20, without any particular fold lines delineated. The rolled template 40 may also be held in its constricted configuration with sutures or a clip, as described above.

FIG. 4 illustrates one method for compressing the flexible annuloplasty ring sizing template 40 into a smaller profile for introduction within the access tube 42. In particular, the flat template 40 is guided lengthwise into a funnel or cone-shaped constrictor 44 which causes the flexible template to bend and then eventually to curl into a spiral shape. By sizing a narrow end 46 of the constrictor 44 the same as or slightly smaller than the access tube 42, the template then can be inserted within the access tube in its spiral configuration. The material of the constrictor 44 may be lubricious, such as Teflon, or the interior of the constrictor may be coated with a lubricious biocompatible material such as used to facilitate passage of intraocular lenses through delivery syringes.

FIG. 5 illustrates an annuloplasty ring sizing template 50 rolled into a tube or spiral and wrapped around a delivery handle 52. The rolled template 50 is secured on the handle 52 using a strap 54 having Velcro ends, though one or more sutures may also be used. This assembly may be inserted into the body with or without using an access tube. Upon delivery of the distal end of the delivery handle 52 to a valve annulus, the surgeon releases the sizing template 50 by removing the strap 54 or cutting or removing sutures as applicable. A separate grasper or other such device may then be used to manipulate the sizing template 50 into the proper orientation within the annulus for a sizing comparison. In one embodiment, an edge of the sizing template 50 may be tethered to the delivery handle 52 to avoid complete detachment of the template while at the same time permitting it to freely move in and around the annulus.

Figure 6B:
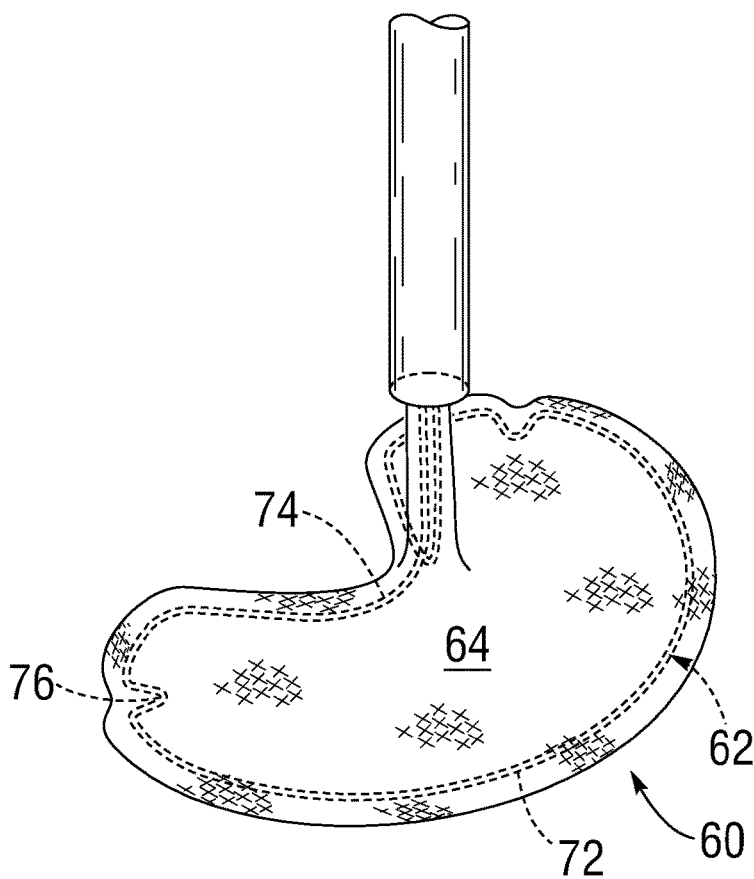
Figure 6C:
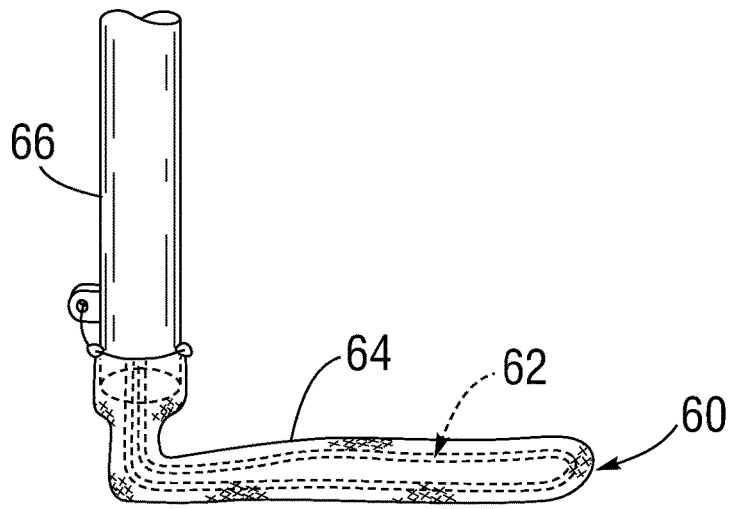

FIGS. 6A-6C show a still further flexible annuloplasty ring sizing template 60 comprising a compressible wireform 62 surrounded by a knit cloth cover 64. The cloth cover 64 attaches to a distal end of an access tube 66 through the use of a suture 68 and eyelet 70, for example, though other attachment means are contemplated. The compressible wireform 62 extends through the access tube 66 in a compressed, generally linear configuration (not shown) and is manipulated longitudinally from a proximal end thereof. Preferably, the wireform 62 is formed of NITINOL. By expelling the wireform 62 from the distal end of the access tube 66, as shown in FIGS. 6B and 6C, the wireform 62 expands and assumes its relaxed shape within the cloth cover 64. In a preferred embodiment, the sizing template 60 assumes a generally planar frame perpendicular to the axis of the access tube 66 and proximal portion of the wireform 62, as seen in FIG. 6C.

In the illustrated embodiment, the wireform 62 expands into the shape of a mitral annulus sizing template, having a convex posterior side 72 opposite a concave anterior side 74, and including a pair of optional trigone notches 76. Although the notches 76 are somewhat occluded by the cloth cover 64, the cover may be formed of a diaphanous material and the wireform 62 may be darkly colored or otherwise colored to contrast with the cloth cover so as to be visible therethrough. Alternatively, the wireform 62 may be radiopaque such that the trigones 76 are visible under fluoroscopy. In any event, the sizing template 60 forms a substantially solid-looking body to be more visible to the surgeon when assessing the size of the surrounding mitral annulus.

In use, the surgeon inserts the access tube 66 into the body through an access port or mini thoracotomy such that its distal end is adjacent the target annulus, and then advances the linearly compressed wireform 62 therethrough. The distal end of the wireform 62 expands within the cloth cover 64 to form the properly shaped sizing template 60. After examining the fit of the sizing template 60 within the mitral annulus by direct visible examination or using a scope, the surgeon then retracts the wireform 62 back into the access tube 66, and removes the entire assembly. A second sizing procedure may be required with a differently-sized template 60 if the surgeon so desires.

FIG. 7A is a perspective view of a still further flexible annuloplasty ring sizing template 80 formed of an elastomeric material and having visibility windows 82. More particularly, the template 80 has the approximate peripheral shape of a mitral annulus with an outer ring defining a convex posterior side 84 and a relatively straight or less convex anterior side 86. Two or more linear spokes 88 extend inward from the outer ring of the template 80 to a generally central hub 90 to which a handle or grasper 92 may be attached. Preferably two spokes 88 are utilized which point generally to the trigone area of the profile of the mitral annulus, thus helping ensure proper orientation of the sizing template 80 upon introduction to the target annulus area. The visibility windows 82 are defined in the spaces between the outer ring and the spokes 88. The material of the template 80 may be opaque or transparent for greater visibility. If the template material is transparent, a highly visible marker line circumscribing the outer periphery may be provided. Furthermore, the marker line may be color-coded to different sizes of annuluses. For instance, a 26 mm template may have a red marker line while a 28 mm template has a purple marker line, and so on.

FIG. 7B is a schematic view of the sizing template 80 being extruded through a compression cone 94, much like the constrictor 44 described above. Although not shown, the sizing template 80 may be constricted to a reduced profile and passed into an access tube, or otherwise secured in its constricted configuration using a suture or other such device.

In use, once the sizing template 80 has been extruded out of the end of an access tube, or otherwise released to assume its relaxed configuration at the target annulus, the handle or grasper 92 may be attached to the central hub 90 for manipulation purposes.

It should be understood that the central hub 90 may take a variety of forms so that different graspers can be connected thereto. For example, the hub 90 may be configured as a generally spherical socket to receive a ball end of a handle (not shown) in a snap-fit configuration to allow for universal rotation of the template 80. In this configuration, the hub 90 may be made from a harder material, such as a harder polymer, then the remainder of the template 80 to permit a secure snap-fit connection. Alternatively, an embedded metal ring around an opening of the hub 90 all the same material as the template 80 may be provided to facilitate the snap-fit connection. Consequently, the hub 90 can be mounted on the remainder of the template 80 using adhesive, ultrasonic welding, or other such attachment means.

FIG. 8 is a perspective view of a solid annuloplasty ring sizing template 100 having an internal skeleton 102 embedded within and more rigid than a surrounding elastomeric template body 104. The skeleton 102 may be formed of a highly elastic polymer or metal such as NITINOL so that it can be compressed into a much smaller profile and advanced through an access tube. Because of the restoring force of the skeleton 102, the template body 104 may be made of a material that is not elastomeric, but instead is merely compressible. However, the elasticity of the inner skeleton 102 permits the template body 104 to alternatively be formed of a transparent non-elastic polymer material, such as a viscoelastic or photoviscoelastic polymeric material like plasticized Polyvinyl Chloride, In one embodiment, the skeleton 102 has a shape much like the sizing template 80 of FIG. 7A, with an outer ring and spokes leading to a central hub 106. As described above, the template 100 may be compressed using a conical constrictor or other such device and held in its constricted configuration within an access tube, or using sutures, a strap or the like. Once expelled from the end of the access tube, or otherwise released, the template 100 assumes its relaxed configuration as seen in FIG. 8. At this point, a handle 108 or other such grasper may be connected to the central hub 106 and used to manipulate the template 100 to size the annulus.

Figure 9:
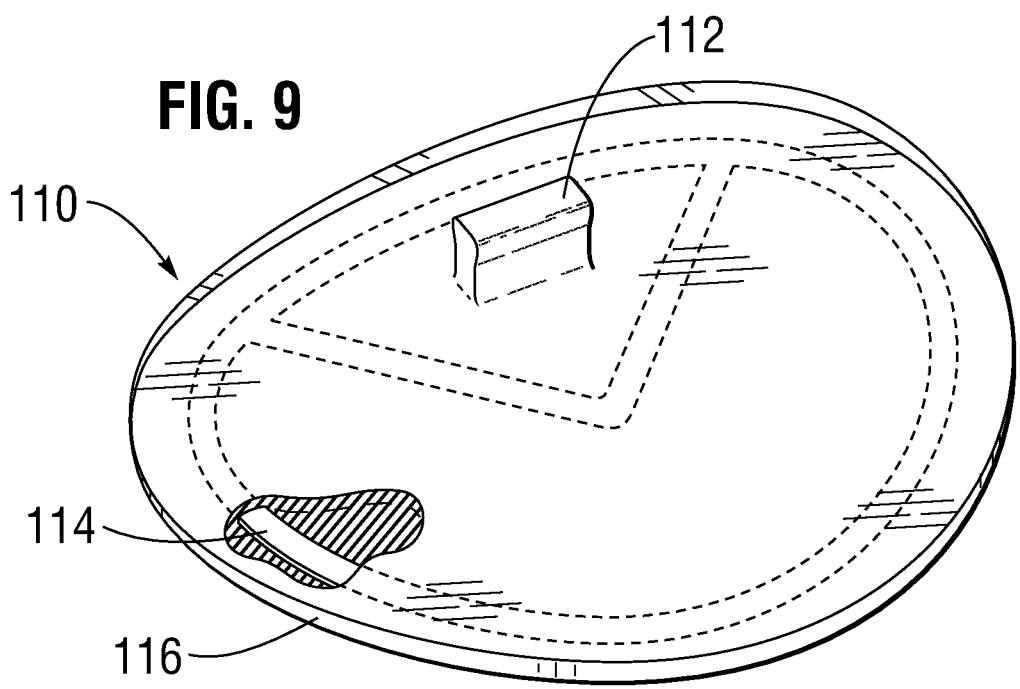
FIG. 9 is a sizing template similar to that shown in FIG. 8 and having a grasping tab extending from one face thereof.

FIG. 9 is a sizing template 110 similar to that shown in FIG. 8 but having a grasping tab 112 extending from one face thereof. The grasping tab 112 projects perpendicularly upward from the generally planar body of the template 110, and may be easily grasped with forceps or other such device, for example robotic end effectors. Preferably, the grasping tab 112 is integrally molded with the elastomeric portion of the template 110. An inner skeleton 114 is shown by a cutaway portion of the elastomeric body 116.

Figure 10:
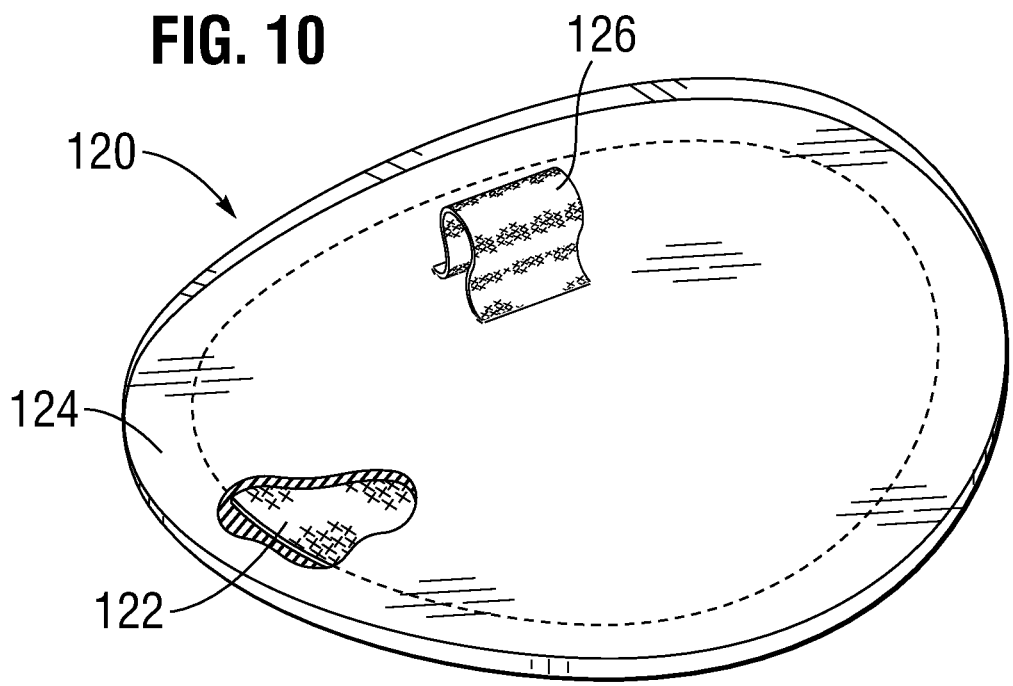
FIG. 10 is a perspective view of a solid annuloplasty ring sizing template having an internal fabric reinforcement member and a fabric grasping tab extending from one face thereof.

Finally, FIG. 10 illustrates a solid annuloplasty ring sizing template 120 having an internal fabric reinforcement member 122 embedded within an elastomeric body 124. The elastomeric body 124 comprises a plate-like member having a periphery sized to approximate the mitral annulus, and the internal fabric reinforcement member 122 is generally planar and sized slightly smaller. A fabric grasping tab 126 extends from one face of the elastomeric body 124 for manipulation by forceps or other such grasper. The grasping tab 126 may be integrally connected with the fabric reinforcement member 122 for strength.

While the invention has been described in its preferred embodiments, it is to be understood that the words which have been used are words of description and not of limitation. Therefore, changes may be made within the appended claims without departing from the true scope of the invention.

What is claimed is:

1. A compressible heart valve annulus sizing template to which a delivery device may be attached for sizing of a heart valve annulus, comprising:
    a plate-like compressible body having a peripheral plan view shape of a target heart valve annulus and a thickness from a proximal to a distal face of between about 0.3-3 mm; and
    an inner skeleton embedded within the compressible body formed of a material more rigid than the material of the compressible body, the inner skeleton comprising an elastic material that may be constricted and provides a restoring force to the surrounding compressible body; and
    an attachment member extending proximally from the proximal face of the compressible body to which a delivery device may be attached for manipulating the template within a human body.

2. The template of claim 1, wherein the inner skeleton comprises an outer peripheral ring in plan view shaped like a target heart valve annulus and a plurality of spokes extending inward therefrom.

3. The template of claim 2, wherein the inner skeleton comprises only two spokes.

4. The template of claim 1, wherein the material of the inner skeleton is selected from a group consisting of a highly elastic polymer and a highly elastic metal.

5. The template of claim 4, wherein the inner skeleton is formed of Nitinol.

6. The template of claim 1, wherein the compressible body is an inelastic polymer.

7. The template of claim 6, wherein the compressible body is a viscoelastic or photoviscoelastic polymer.

8. The template of claim 6, wherein the compressible body is transparent.

9. The template of claim 1, wherein the compressible body is elastomeric.

10. The template of claim 1, wherein the compressible body comprises a solid member extending across a periphery thereof.

11. The template of claim 10, wherein the attachment member comprises a grasping tab integrally molded with the compressible body and extending from the proximal face thereof.

12. The template of claim 1, wherein the compressible body is transparent.

\* \* \* \* \*